US010825555B2

(12) United States Patent
Thiese et al.

(10) Patent No.: US 10,825,555 B2
(45) Date of Patent: Nov. 3, 2020

(54) SYSTEMS AND METHODS FOR MANAGING A DATABASE DURING AN EXAMINATION

(71) Applicant: SafeLane Health, Inc., Salt Lake City, UT (US)

(72) Inventors: Matthew S. Thiese, Salt Lake City, UT (US); Kurt T. Hegmann, Salt Lake City, UT (US); Joseph F. D'Alessandro, Salt Lake City, UT (US); Meghann A. Kopecky, Salt Lake City, UT (US)

(73) Assignee: Safe Lane Health, Inc., Salt Lake City, UT (US)

( * ) Notice: Subject to any disclaimer, the term of this patent is extended or adjusted under 35 U.S.C. 154(b) by 394 days.

(21) Appl. No.: 15/451,018

(22) Filed: Mar. 6, 2017

(65) Prior Publication Data
US 2017/0262618 A1 Sep. 14, 2017

Related U.S. Application Data

(60) Provisional application No. 62/306,960, filed on Mar. 11, 2016.

(51) Int. Cl.
| | |
|---|---|
| *G16H 10/20* | (2018.01) |
| *G09B 7/06* | (2006.01) |
| *G06F 16/22* | (2019.01) |
| *G06F 16/23* | (2019.01) |
| *G06F 19/00* | (2018.01) |

(52) U.S. Cl.
CPC ......... *G16H 10/20* (2018.01); *G06F 16/2282* (2019.01); *G06F 16/2379* (2019.01); *G06F 19/00* (2013.01); *G09B 7/06* (2013.01)

(58) Field of Classification Search
CPC .. G06F 16/2379; G06F 16/2282; G06F 19/00; G16H 10/20; G09B 7/06
See application file for complete search history.

(56) References Cited

U.S. PATENT DOCUMENTS

| | | | | |
|---|---|---|---|---|
| 8,060,378 B2 * | 11/2011 | Iliff | ..................... | G06F 19/3418 705/2 |
| 8,429,547 B2 * | 4/2013 | Hussam | ................. | G06Q 10/10 715/763 |
| 2002/0077860 A1 * | 6/2002 | Earnest | .................. | G06Q 30/02 705/3 |

(Continued)

FOREIGN PATENT DOCUMENTS

WO WO-0209004 A1 * 1/2002 ......... G06F 19/3418

OTHER PUBLICATIONS

FMCSA, Federal Motor Carrier Safety Administration, Medical Applications and Forms, https://www.fmcsa.dot.gov/medical/driver-medical-requirements/medical-applications-and-forms, visited Feb. 16, 2016, 2 pages.

(Continued)

*Primary Examiner* — Aryan E Weisenfeld
*Assistant Examiner* — Steven G Sanghera
(74) *Attorney, Agent, or Firm* — TraskBritt (57) ABSTRACT

Systems and methods are provided for managing a database. The systems and methods described maybe used to efficiently utilize computing resources, including at a handheld device, to provide questions and recommendations during a medical examination.

20 Claims, 3 Drawing Sheets

(56) References Cited

U.S. PATENT DOCUMENTS

| | | | | |
|---|---|---|---|---|
| 2003/0135095 A1* | 7/2003 | Iliff | ................ | A61B 5/0002 |
| | | | | 600/300 |
| 2004/0122709 A1* | 6/2004 | Avinash | ............ | G06F 19/3418 |
| | | | | 705/2 |
| 2005/0273359 A1* | 12/2005 | Young | .................. | G06Q 50/22 |
| | | | | 705/2 |
| 2009/0125331 A1* | 5/2009 | Pamsgaard | .......... | A61K 31/343 |
| | | | | 705/3 |
| 2012/0054644 A1* | 3/2012 | Venkataraman | ....... | G06Q 50/20 |
| | | | | 715/753 |
| 2013/0103414 A1* | 4/2013 | Eng | ...................... | A61B 5/486 |
| | | | | 705/2 |

OTHER PUBLICATIONS

U.S. Department of Transportation Federal Motor Carrier Safety Administration, Form MCSA-5876, Medical Examiner's Certificate (for Commercial Driver Medical Certification), U.S. Department of Transportation Federal Motor Carrier Safety Administration, visited Feb. 16, 2016, 1 page.

U.S. Deparment of Transportation Federal Motor Carrier Safety Administration, Form MCSA-5875, Medical Examination Report Form (for Commercial Driver Medical Certification), https://www.fmcsa.dot.gov/sites/fmcsa.dot.gov/files/docs/MedicalExaminationReportForm_091616_MCSA_5875.pdf, visited Feb. 16, 2016, 9 pages.

* cited by examiner

SYSTEMS AND METHODS FOR MANAGING A DATABASE DURING AN EXAMINATION

CROSS-REFERENCE TO RELATED APPLICATION

This application claims the benefit of U.S. Provisional Patent Application Ser. No. 62/306,960, filed Mar. 11, 2016, the disclosure of which is hereby incorporated herein in its entirety by this reference.

TECHNICAL FIELD

The application relates generally to systems and methods for managing databases. In particular, the systems and methods described herein may facilitate efficient utilization of computing resources while conducting a medical examination.

BACKGROUND

Driving a commercial motor vehicle (CMV) generally requires a higher level of knowledge, experience, skills, and physical abilities than that required to drive a non-commercial vehicle. In order to obtain a commercial driver's license (CDL), an applicant must pass both skills and knowledge testing geared to these higher standards. Similarly, other safety sensitive jobs (e.g., forklift driving, overhead crane operation, work at heights, electricians, nuclear workers, other transportation modes) require comparable knowledge, experience, skills and physical abilities to safely execute the job tasks.

To provide the medical testing to applicants wanting to become or maintain their status as commercial motor vehicle (CMV) drivers, the National Registry of Certified Medical Examiners was developed and is managed and maintained by the Federal Motor Carrier Safety Administration (FMCSA). The Federal Motor Carrier Safety Regulations (FMCSRs) require that commercial motor vehicle (CMV) drivers comply with physical qualification requirements and be examined and certified by a medical examiner at least once every two years. The National Registry program ensures that medical examiners that perform Department of Transportation (DOT) driver medical examinations are properly trained and certified by FMCSA to do so.

Generally, comparable regulations for other safety sensitive jobs do not widely exist and there are generally no specified forms to be used for the physical examinations for those safety sensitive jobs. Thus, the FMCSA requirements are often relied upon to determine fitness for work for these other types of safety sensitive jobs.

Conventionally, applicants wanting to become or maintain their status as commercial motor vehicle (CMV) drivers visit the medical examiner's office and are given a clipboard with a paper form on it and asked to fill it out. The paper form provided to the applicant is generally a standardized federal form (i.e., the Medical Examination Report (MER) Form, MCSA-5875, available online at: https://www.fmcsa.dot.gov/medical/driver-medical-requirements/medical-applications-and-forms) that must be filled out by hand. However, with the standardized paper form, applicants often do not fill out the form completely and/or some answers on the standardized form may be illegible. After filling out the form, the applicant is examined by the medical examiner. However, there are often multiple additional questions that should be asked by the medical examiner to find out more information about the applicant's medical history and conditions. Often (as high as 50% of the time) the medical examiner, may need to request additional information or documentation from the driver. This requires that the driver go get that documentation or a signed letter from one or more of their treating physicians. They then reschedule and return to that examiner to have a final determination regarding their medical certification. The medical certification determination is based on the multiple sources of guidance provided by FMCSA and other entities, as well as the training and medical opinion of the examiner. These sources of guidance may be from documents that are more than thirty years old. This guidance is difficult to identify, interpret, and follow in an efficient manner. Failure to follow guidance opens examiners and companies to lawsuits. However, the ultimate medical certification determination is limited by the questions asked by the medical examiner and the information available to the medical examiner at the time of the examination. Generally, the criteria or guidelines for properly evaluating an applicant are not readily accessible or even easy for the medical examiner to find and have for reference during an examination.

If the applicants are medically certified, they are given a medical examiner's certificate, which gives the applicant a period of up to two years where the applicant is considered safe to perform their safety sensitive job. The examiner also has to communicate to FMCSA who they examined and the medical certification determination within twenty-four hours through an online portal.

Until being certified or recertified, the applicant cannot operate a commercial motor vehicle. Often, a company that employs the applicant is paying for this exam. These companies have differing levels of access to these data, with some only wanting the medical certification and date of expiration, while others house the paper form. The office of the medical examiner also houses the paper form.

In view of the above, it can be seen that there are many inefficiencies in the standardized paper-based form system that often results in incomplete information from the applicant, the medical examiners having to seek out guidance that is not readily available, difficulties in accessing and sharing documents between the medical examiners, the FMCSA, the applicants, and the companies they may work for, and lost productivity for the examiner, driver, and company.

BRIEF SUMMARY

Embodiments of the disclosure include systems and methods for managing a database for a medical examination. Such a system may include a non-transitory computer-readable storage medium, an electronic display, and a processor operably coupled with the electronic display and the storage medium. The non-transitory computer-readable storage medium may store at least one database and at least one software application. The processor may be configured to, upon execution of the software application: display a user interface on the electronic display; select an initial set of medical questions from a first table of the at least one database; insert the initial set of medical questions into a second table of the at least one database; present at the displayed user interface one or more of the initial set of medical questions stored in the second table; continually update the initial set of medical questions stored in the second table based on one or more answers responsive to the initial set of medical questions; present at the displayed user interface one or more of the continually updated initial set of medical questions stored in the second table; and store answers responsive to the displayed initial set of medical questions in at least one database.

The processor may be further configured to, upon execution of the software application: responsive to storing the answers responsive to the displayed initial set of medical questions in at least one database, select a second set of medical questions from the first table and insert the second set of medical questions into the second table; present at the displayed user interface one or more of the second set of medical questions stored in the second table; continually update the second set of medical questions stored in the second table based on one or more answers responsive to the second set of medical questions; present at the displayed user interface one or more of the continually updated second set of medical questions stored in the second table; store in at least one database answers responsive to one or more of the second set of medical questions and the answers responsive to the continually updated second set of medical questions; evaluate the stored answers based on stored medical data; and present at the displayed user interface one or more recommendations for examination based on the stored answers.

Embodiments of the disclosure further include systems and methods for managing a database for a medical examination. Such a system may include a non-transitory computer-readable storage medium, an electronic display, and a processor operably coupled with the electronic display and the storage medium. The non-transitory computer-readable storage medium may store at least one database and at least one software application. The processor may be configured to, upon execution of the software application: display a user interface on the electronic display; select an initial set of medical questions from the at least one database; insert the initial set of medical questions into a table of the at least one database; present at the displayed user interface one or more of the initial set of medical questions stored in the table; continually update the initial set of medical questions stored in the table based on one or more answers responsive to the initial set of medical questions; present at the displayed user interface one or more of the continually updated initial set of medical questions stored in the table; and store answers responsive to the displayed initial set of medical questions in at least one database.

Embodiments of the disclosure further include a method of managing a database for a medical examination. Such a method may include selecting a set of medical questions from medical questions stored at a first table of the at least one database; inserting the set of medical questions into a second table of the at least one database; continually updating the medical questions stored in the second table based on one or more answers responsive to the initial set of medical questions; and storing the responsive answers in at least one database.

The foregoing and other features and advantages of the present disclosure will be made more apparent from the descriptions, drawings, and claims that follow. One of ordinary skill in the art, based on this disclosure, would understand that other aspects and advantages of the present disclosure exist.

BRIEF DESCRIPTION OF THE DRAWINGS

The purpose and advantages of the present invention will be apparent to one of ordinary skill in the art from the summary in conjunction with the following appended Figures.

DETAILED DESCRIPTION

In the following detailed description, reference is made to the accompanying drawings which form a part hereof, and in which is illustrated specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions, rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus or all operations of a particular method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It should be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented or performed with a processor, such as a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A processor herein may be any processor, controller, microcontroller, or state machine suitable for carrying out processes of the disclosure. A processor may also be implemented as a combination of computing devices, such as a combination of a DSP and a microprocessor, a plurality of microprocessors, one or more microprocessors in conjunction with a DSP core, or any other such configuration. When configured according to embodiments of the disclosure, a special-purpose computer improves the function of a general-purpose computer because, absent the disclosure, the general-purpose computer would not be able to carry out the processes of the disclosure.

The disclosure also provides meaningful limitations in one or more particular technical environments that go beyond an abstract idea. For example, embodiments of the disclosure provide improvements in the field of medical evaluation of applicants wanting to become or maintain their status as commercial motor vehicle (CMV) drivers, and other related fields. In particular, embodiments may improve the ability of medical examiners to efficiently and completely determine and evaluate one or more medical conditions of the applicant by providing a system that can actively adapt to answers from the applicant and other medical data input into the system regarding the applicants. The system can further assist in guiding the medical examiner in the examination of the applicant. As detailed below, embodiments of the instant disclosure act to guide the medical examiner in the examination of the applicant through automation of the exam protocol and display guidance and underlying source(s) for the medical examiner's reference.

Embodiments of the disclosure may facilitate the efficient use of computing resources and data transmission (e.g., bandwidth and throughput) resources while providing a platform that enables the complete evaluation of medical conditions. The system may draw on information in one or more databases while limiting the data set used during an examination to the data best understood to be relevant at a given time. Among other things, the efficient data management may enable the platform to be compatible with handheld devices, for example, tablets and mobile phones, be delivered using a client/server arrangement, and/or delivered as a web-application through a browser.

The system can compile, store, evaluate, and output data relating to the applicant such that the data can be easily evaluated and communicated as needed.

It is noted that while embodiments of the instant disclosure are described herein with particular reference to applicants wanting to become or maintain their status as commercial motor vehicle (CMV) drivers, the disclosure in not so limited and may include evaluation of one or more subjects for other purposes. For example, embodiments of the instant disclosure may be utilized to evaluate applicants for other safety sensitive jobs (e.g., a job having a relatively higher risks of causing injury to the subject, injury to others, or to surrounding property), such as, for example, forklift drivers, overhead crane operators, workers that operate at heights, electricians, nuclear workers, oil rig workers, military personnel, other transportation workers (e.g., locomotive operators or engineers, aircraft pilots), etc. Further, embodiments of the instant disclosure may be utilized to provide health assessments or screening for general subjects or patients (e.g., for life insurance evaluation, general physical evaluations, etc.).

In addition, it is noted that the embodiments may be described in terms of a protocol and/or a process and may be depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be rearranged. A protocol and a process may correspond to a method, a function, a procedure, a subroutine, a subprogram, interfacing with an operating system, etc. Furthermore, the methods disclosed herein may be implemented in hardware, software, or both. If implemented in software, the functions may be stored or transmitted as one or more instructions (e.g., software code) on a non-transitory computer-readable medium. Non-transitory computer-readable media includes both computer storage media and communication media including any medium that facilitates transfer of a computer program from one place to another. In various embodiments described in this disclosure, the software may be executed by one or more central processing units operating in a general purpose computer, and the non-transitory computer-readable mediums may include random-access-memory (RAM), system memory and registers, flash memory, hard-drives, and combinations thereof. When executing software the general purpose computer may be thought of as a specific purpose computer.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise a set of elements may comprise one or more elements.

Figure 1:
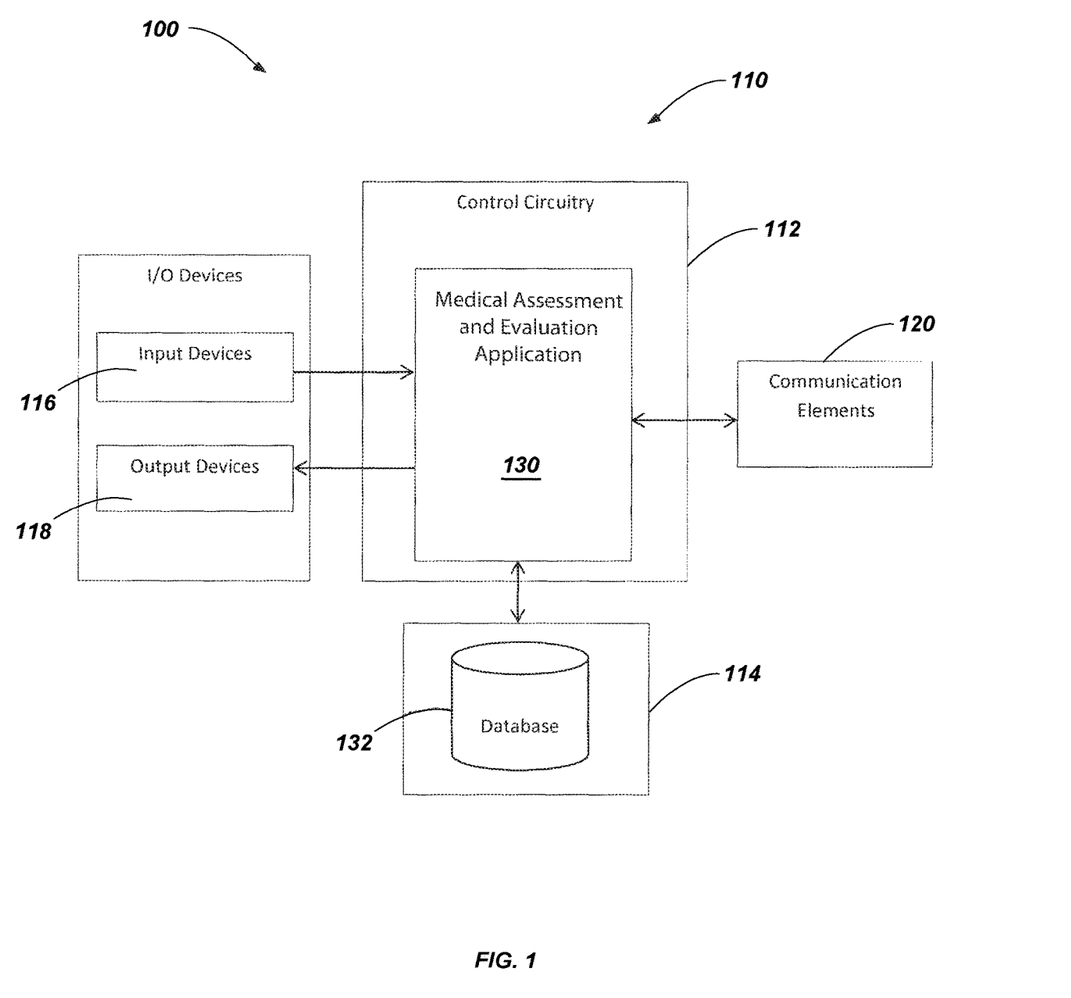
FIG. 1 is a simplified block diagram of an example of a medical assessment and evaluation system according to an embodiment of the present disclosure.

FIG. 1 is a simplified block diagram of a medical assessment and evaluation system 100 (or portion thereof) of an applicant for a commercial motor vehicle (CMV) driver certification. For example, the system 100 may include a user device 110 used by a medical examiner or other practitioner (or the applicant) to provide a medical assessment and evaluation of the applicant. While one input device 116 is depicted in FIG. 1, multiple input devices 116 may be provided with the system 100 for use by multiple medical examiners, other practitioners, office personal, and/or the applicant to, for example, enter information into the system 100 and/or receive information from the system 100. The user device 110 may include control circuitry 112 operably coupled to one or more storage devices 114 (hereinafter referred to as storage device), I/O devices (input devices 116, output devices 118) configured to enable user interactions with the user device 110, and communication elements 120 configured to enable the user device 110 to communicate over networks with other devices (e.g., servers, other user devices, etc.). Networks may include a local area network (LAN), a wide-area network (WAN), the Internet, mobile wireless networks, other suitable networks, or combinations thereof.

The control circuitry 112 may include a memory device and a processor. The control circuitry 112 may be configured to execute an operating system. By way of non-limiting example, the operating system may include ANDROID®, iOS®, Windows Phone, Microsoft Windows, Apple OS X®, UNIX®, LINUX®, and other operating systems. The control circuitry 112 may include various application programs (hereinafter "apps") configured to function in an environment provided by the operating system. For example, the control circuitry 112 may include a medical assessment and evaluation application 130, which may be executed by the processor according to computer-readable instructions stored in memory of the storage device 114. In other words, the computer-readable instructions may be configured to instruct the control circuitry 112 to perform the functions discussed in more detail below. The computer-readable instructions may be provided to the user device 110 via a software distribution server having the computer-readable instructions stored thereon.

The input devices 116 may be configured to enable a user to interact with an interface of the application 130, such as to provide inputs (e.g., text inputs, video inputs, audio inputs, etc.) into the system 100. For example, the input devices 116 may include a keyboard, microphone, camera, etc. Output devices 118 may be configured to convey information to the user from the application 130, such as to provide outputs (e.g., text outputs, video outputs, audio outputs, etc.) from the system 100. For example, the output devices 118 may include electronic displays, speakers, etc. In some embodiments, some aspects of input devices 116 and output devices 118 may be integrally formed (e.g., touch screen display).

The storage device 114 may include a database 132 stored in memory thereof. The database 132 may include the evaluation materials, screening questions, recorded entries, and related data that are provided to and/or generated by the user during use of the application 130.

The user device 110 may include smart phones, tablet computers, handheld computers, laptop computers, desktop computers, smart televisions, and other similar devices configured to deliver content to a user. While discussion herein is primarily focused on embodiments that include an "app" on a handheld computer device or an application running on a local laptop or desktop computer, it is contemplated that web-based embodiments that are accessible by web-browsers or other similar user interfaces are also within the scope of the present disclosure. Thus, rather than having the application 130 stored locally on the user device 110, the application 130 may be stored on a remote server that is accessed by the user device 110. The database 132 may be maintained by the remote server in such an embodiment, which may also maintain the databases for a plurality of different user devices. In some embodiments, at least a portion of the database 132 may be stored both locally on the user device 110 with some data also being stored remotely.

Figure 2:
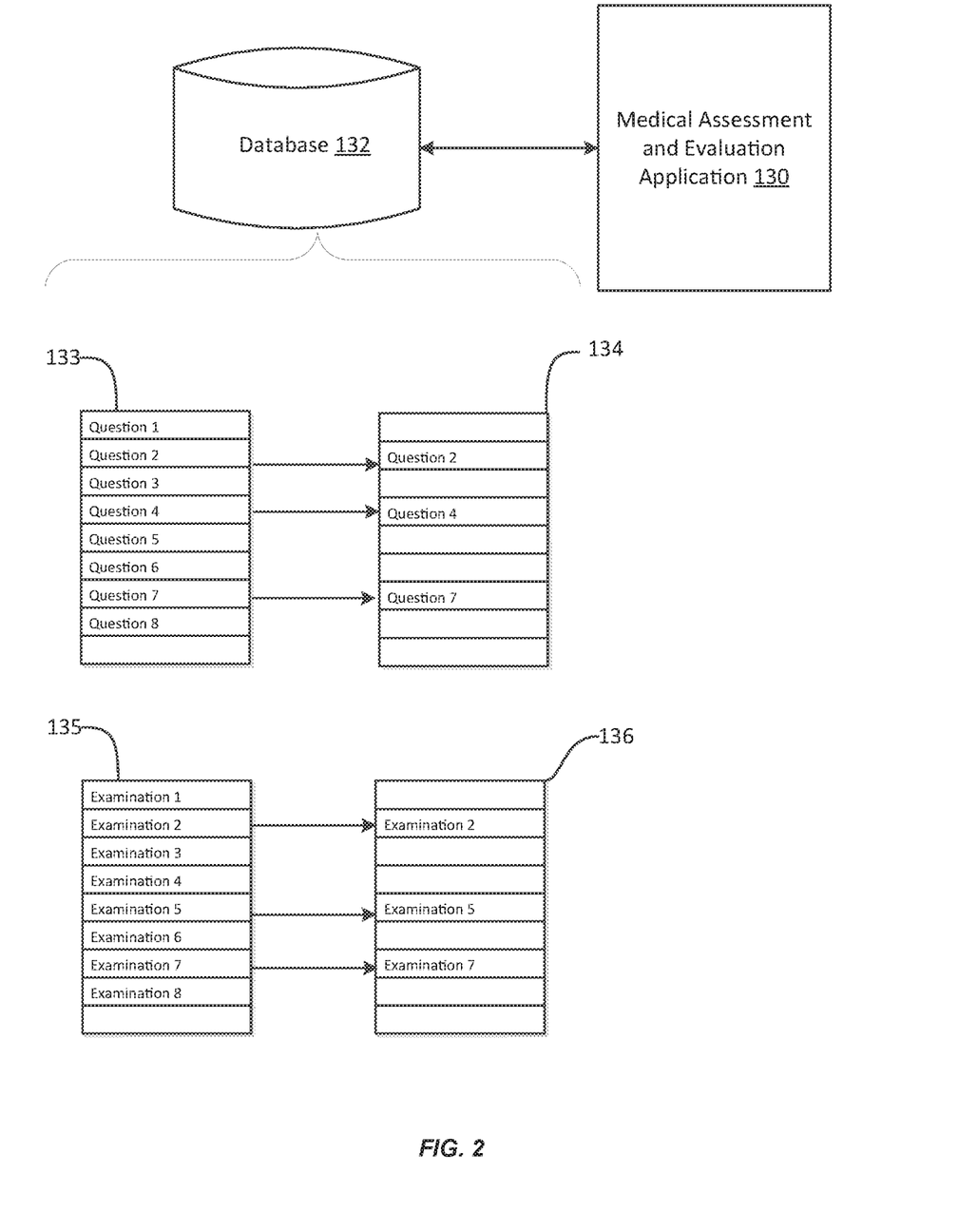
FIG. 2 is a simplified block diagram that illustrates a database and software application for management the database according to an embodiment of the present disclosure.

FIG. 2 is a block diagram of the database 132 and the application 130, according to an embodiment of the disclosure. The database 132 may include, among other things, screening questions stored in table 133 and exam procedures stored in table 135. In some embodiments, the screening questions stored in table 133 and exam procedures stored in table 135 may be updated from external sources with new questions and procedures, and old questions and procedures may be culled. The table 134 may include a subset (or references to a subset) of the medical screening questions in table 133. The table 134 may be updated during an exam by the application 130, for example, questions may be added and removed from the table 134. In some embodiments, the order of the questions in table 134 may reflect the exam being administered and questions and procedures may be re-ordered based on answers given by the applicant. Similarly the table 136 may include a subset of the examination procedures stored in table 135. The table 136 may be update during a medical examination by the application 130, for example, examination procedures may be inserted and deleted from the table 136.

Figure 3:
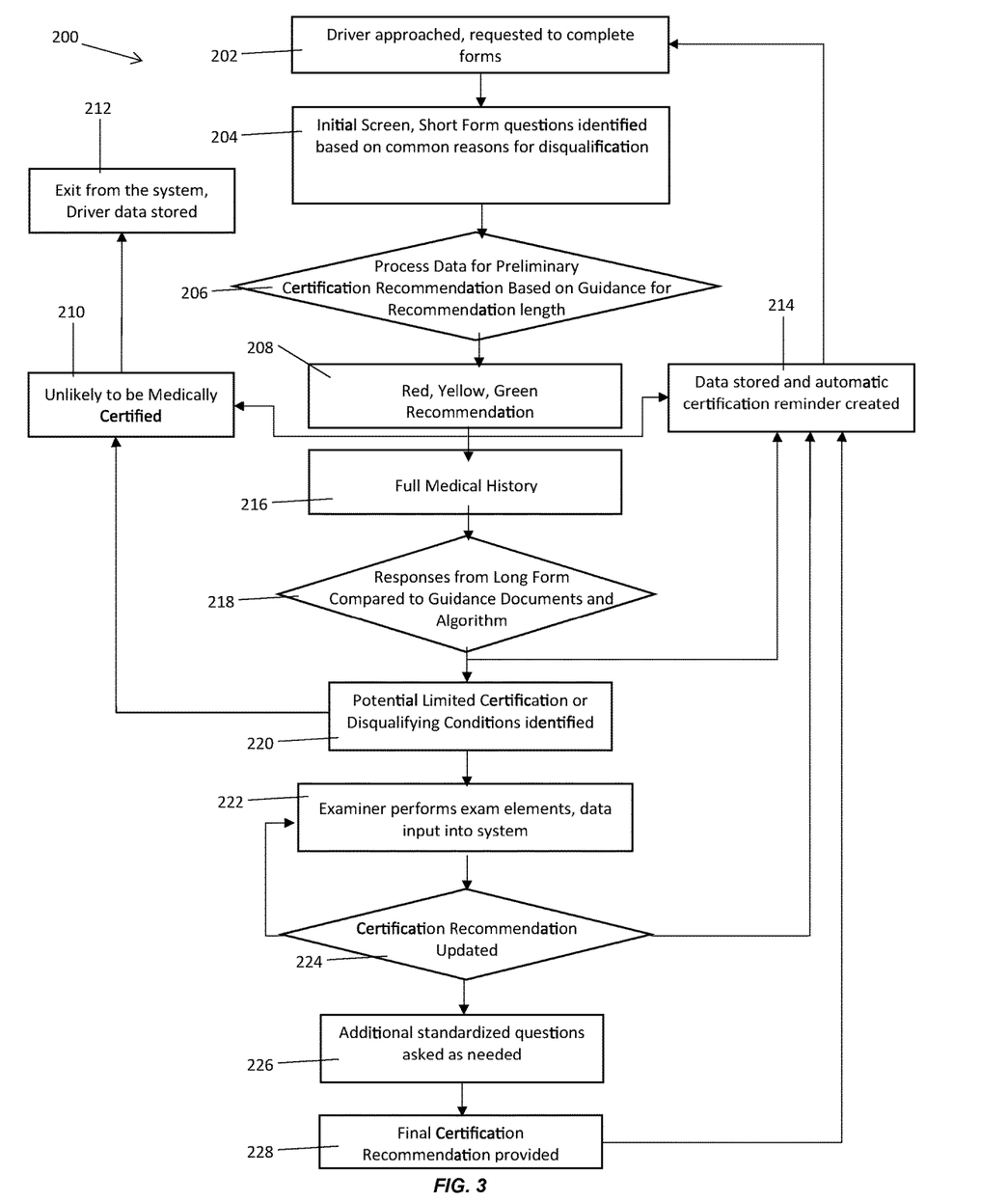
FIG. 3 is a flowchart illustrating a method of determining and evaluating a medical condition of a potential commercial motor vehicle driver according to an embodiment of the present disclosure.

FIG. 3 is a flowchart 200 illustrating a method of determining and evaluating a medical condition of a potential commercial motor vehicle driver according to an embodiment of the present disclosure. Referring to FIGS. 1, 2, and 3 at operation 202, an applicant wanting to become or maintain their status as a commercial motor vehicle (CMV) driver is provided with one or more forms (e.g., questionnaires) to input the identity of the applicant into the system 100. For example, in response to the input of the information from the identify forms, a driver profile may be automatically created within the system 100 and auto-populated with driver demographic and contact information. In some embodiments, the identify forms may be provided on the user device 110 and input directly into the system 100 by a user (e.g., the applicant, medical examiner, or other practitioners). In additional embodiments, the identity forms may be completed manually and then entered into the system 100 by the user.

It should be appreciated that any task being described herein as performed by medical examiner or practitioner, in some instances, may also be performed by other assistants, support staff, or office staff working with the medical examiner or practitioner.

In some embodiments, the user device 110 utilized (e.g., by the applicant or the medical practitioner) to answer the questionnaires and enter personal information of the applicant may be the same user device 110 that the medical practitioner utilizes to review the data from the system 100 based on the questionnaires and utilizes to input further data from a physical exam or additional in-person questions, as discussed below. In additional embodiments, multiple user devices 110 may be utilized. For example, one user device 110 may be utilized to answer the questionnaires and enter personal information of the applicant and another user device 110 may be utilized by the medical practitioner to review the data from the system 100 based on the questionnaires and to input further data from a physical exam or additional in-person questions.

In some embodiments, the system 100 may receive data regarding the applicant from a network. For example, data from companies that employ potential applicants, data from medical examiners (e.g., data relating to the need to reevaluate a current driver due to a known medical condition and/or a selected period of time passing), and/or data from the applicant's previous examination(s) stored within the system 100 may act to notify a user of the system 100 of the need for a medical examination of an applicant. In some embodiments, the system 100 may send alerts to the medical practitioner and/or the applicant as a reminder that a medical evaluation is due.

In some embodiments, the system 100 may select a subset of available medical screening questions relevant to the applicant and the exam. The subset of medical screening questions may be selected based on an applicant profile, a type of commercial license, requirements of an entity administering the exam, and combinations thereof. In some embodiments, the subset of questions may be selected from medical screening questions stored in the database 132. While all the available medical screening questions may be stored on the database 132, in some embodiments questions may be stored remotely, for example, in a public database, and received at the system 100 to be part of the available medical screening questions from which the subset of medical screening questions is selected. In some embodiments, the subset of available medical screening questions, or references to the subset of questions, may be stored in the table 133 or another database.

At operation 204, once the applicant's identity is stored in the system 100, the system 100 may provide an initial set of medical screening questions (e.g., questionnaires) to the applicant. The initial set of medical screening questions may be the subset of medical screening questions, or it may be a part of the subset of medical screening questions. The initial set of questions may be stored in the table 134. The initial set of medical screening questions may be provided on the user device 110 and answers to the questions may be input directly into the system 100 (e.g., via the user device 110) by one or more of the medical practitioner and the applicant. For example, the initial set of medical screening questions provided to the applicant on the user device 110 from the system 100 may be based on common reasons for disqualification identified from peer-reviewed literature and professional experience. The initial set of medical screening questions may provide an initial screen of the most common and definitive medical issues that have recommendations against medical certification for a commercial driver license (CDL).

In some embodiments, the initial set of medical screening questions may be administered to the system 100 to automatically skip selected questions and/or introduce additional questions based on previous responses of the applicant or other information provided to the system 100 (e.g., based on demographic information regarding the applicant acquired at operation 202). For example, if the applicant answers "no" to a particular question, the system 100 may automatically omit one or more related questions in a subset based on the previous response. In one embodiment, the omitted question(s) may be removed from the table 134. If the applicant answers "yes," another select response (e.g., "unknown"), or has not provided a response to one or more questions, the system 100 may automatically insert and present additional questions to gather information to further assist in quantifying the medical history of the applicant. In one embodiment, the additional questions may be inserted into the table 134. The system 100, and more particularly the software application 130, may include questionnaire protocols to determine whether to skip or omit questions. The questionnaire protocol may be indicative of guidelines for medical examination questionnaires as well as incorporate a priori information about the relevance of various questions to each other, including whether an answer to a question in the table 134 renders other questions irrelevant.

In some embodiments, the system 100 may automatically insert additional questions into the table 134 and present the additional questions to the applicant if the selected responses by the applicant are otherwise flagged by the system 100 as defined by a set of rules, for example, in the questionnaire protocol, in the system 100. For example, the system 100 may automatically insert and present additional questions if the selected responses by the applicant are identified as being inconsistent relative to each other to gather information to further assist in quantifying the medical history of the applicant. By way of further example, the system 100 may automatically insert and present additional questions based on other information already present in the system 100 regarding the applicant (e.g., based on responses from previous questions, based on results from previous medical examinations, and/or based on demographic information regarding the applicant acquired at operation 202).

At operation 206, once the applicant has completed the initial set of medical screening questions, the system 100 may automatically score the initial set of medical screening questions based on the applicant's responses based on a computerized algorithm. For example, each of the responses and related questions may be programmed in the system 100 to have a selected value or weight (e.g., a numerical value) in order to provide a total score for the applicant. In some embodiments, the questions and related responses may be weighted based off available peer-reviewed publications and other guidance, where such guidance is regularly updated within the system 100. For example, responses and questions relating to factors that may be relatively more likely to disqualify an applicant from obtaining or maintaining medical certification for a commercial driver license (e.g., be relatively more likely to effect the applicant's ability to regularly operate a commercial motor vehicle) will be scored relatively higher than questions and responses that are relatively less likely to effect the applicant's ability to operate a commercial motor vehicle.

In some embodiments, the system 100 may also provide a recommendation on the period of time before another medical examination is or should be required for the applicant based on the applicant's responses to the initial set of screening questions (e.g., a recommendation length).

At operation 208, once the responses from these questions are automatically scored by the system 100 using the predetermined computerized algorithm, a value is provided (e.g., on the user device 110). In some embodiments, the system 100 may automatically categorize the numerical value into two or more regions to indicate the probability of the applicant being able to ultimately pass the full medical examination, discussed below. For example, the system 100 may automatically categorize the numerical value in a red region, a yellow region, or a green region to indicate whether further examination is likely to result in the applicant passing (e.g., the green region), whether further examination might or might not result in the applicant passing (e.g., the yellow region), or whether further examination is likely to not result in the applicant passing (e.g., the red region) along with a recommendation that the examination should be terminated at this juncture (e.g., at operations 210 and 212), if applicable. In some embodiments, the numerical value or the category assigned to the numerical value may be utilized by the system 100 to formulate the content of the full medical examination, discussed below.

The system 100 may take the data from the initial set of medical screening questions and store (e.g., associate) that data with the applicant's profile (e.g., at operations 212 and 214). In some embodiments, at operation 214, computerized reminders may be created in the system 100 regarding the applicant's profile (e.g., reminders of when to continue the medical examination, reminders to check on updates in the applicant's medical history, etc.). For example, a reminder regarding an applicant who has been identified by the system 100 as not being able to proceed with the full medical examination may be created if the system 100 identifies that the applicant may be able to proceed with the full medical examination after the occurrence of a selected event (e.g., a select future medical diagnosis, a selected period of time, etc.).

At operation 216, the system 100 may proceed with a full set of medical history questions of an applicant who has been cleared by the system 100 in the initial set of medical screening questions. In some embodiments, available questions for the full set of medical history questions may be stored in the database 132 and table 133. The application 130 may select the set of medical history questions for the applicant and store them in table 134. The questions may be selected based on, for example, the answers provided during the initial screening, an applicant profile, a type of commercial license, requirements of an entity administering the exam, and combinations thereof. In some embodiments, the full medical history may be administered by the system 100 based on the entity who is requesting the commercial driver medical exam (CDME). For example, the system 100 may be preprogrammed (e.g., with multiple question sets that are selected by the system 100, selected sequencing and the selected addition and/or removal of questions based on previous responses in a question set, etc.) based on the requesting entity. By way of further example, the system 100 may be preprogrammed with multiple question sets including a question set based on the minimum requirement mandated by the Federal Motor Carrier Safety Administration (FMCSA) or additional question sets that include a longer questionnaire of probing questions and computerized skip sequences, which automatically skip questions based on prior responses. The guidelines and requirements may be captured as the questionnaire protocol(s) and/or rules engine(s) of the application 130. In some embodiments, the longer question sets may include questions that are tailored to obtain the most relevant medical information regarding medical certification or less lengthy question sets that include the FMCSA required questions and select additional probing questions and corresponding automated skip sequences.

In some embodiments, the system 100 may be programmed to take the data received and recorded in the initial examination and automatically fill out selected corresponding questions in the full set of medical screening questions. For example, after populating the table 134 with the full set of medical screening questions, the application 130 may "answer" questions with data corresponding to the answers provided during the initial medical screening. As questions are answered, they may be removed from the table 134 as well as other questions that are no longer relevant. New questions may be inserted into the table 134 based on the corresponding data.

In some embodiments, the system 100 may be programmed to take the data received in the full medical history and automatically fill out a form to be outputted from the system 100. For example, the system 100 may be programmed to take the data received in one or both of the initial and full medical history and automatically fill out the standard form required by FMCSA and output or send (e.g., upload) that form to the applicant, medical practitioner, or requesting entity (e.g., in a PDF format). In some embodiments, the system 100 may also enable the applicant to electronically sign the created form.

As above, the full set of medical screening questions may be administered to the system 100 to automatically skip selected questions and/or introduce additional questions based on previous responses of the applicant, the questionnaire protocol, and/or other information provided to the system 100 (e.g., based on demographic information regarding the applicant acquired at operation 202). For example, if the applicant answers "no" to a particular question, the system 100 may automatically omit one or more related questions in a subset based on the previous response. If the applicant answers "yes," another select response (e.g., "unknown"), or has not provided a response to one or more questions, the system 100 may automatically insert and present additional questions to gather information to further assist in quantifying the medical history of the applicant. In some embodiments, the omitted/skipped questions are removed from the table 134. New questions may be inserted into the table 134. This manner, the table 134 is updated and current with the questions being administered in the exam.

In some embodiments, the system 100 may automatically insert additional questions into the table 134 and present the additional questions to the applicant if the selected responses by the applicant are otherwise flagged by the system 100 as defined by a set of rules, for example, the questionnaire protocol, in the system 100. For example, the system 100 may automatically insert and present additional questions if the selected responses by the applicant are identified as being inconsistent relative to each other to gather information to further assist in quantifying the medical history of the applicant. By way of further example, the system 100 may automatically insert and present additional questions based on other information already present in the system 100 regarding the applicant (e.g., based on responses from previous questions, based on results from previous medical examinations, based on responses received in the initial set of medical screening questions at operation 204, and/or based on demographic information regarding the applicant acquired at operation 202).

In some embodiments, the applicant's responses are stored in fields of the table 134 of the database 132. The final table 134, therefore, may be stored in the database 132 (or another database) as a record of the examination and answers provided by the applicant, as well as the applicant's profile and other information about the applicant's exam and license.

At operation 218, once the applicant has completed the full set of medical screening questions, the system 100 may automatically score the full set of medical screening questions based on the applicant's responses based on a computerized algorithm (e.g., a second algorithm that is distinct from the algorithm utilized in the initial screening). For example, each of the responses and related questions may be programmed in the system 100 to have a selected value or weight (e.g., a numerical value) in order to provide a total score for the applicant. In some embodiments, the questions and related responses may be weighted based off available peer-reviewed publications and other guidance, where such guidance is regularly updated within the system 100. For example, responses and questions relating to factors that may be relatively more likely to disqualify an applicant from obtaining or maintaining medical certification for a commercial driver license (e.g., be relatively more likely to effect the applicant's ability to regularly operate a commercial motor vehicle) will be scored relatively higher than questions and responses that are relatively less likely to effect the applicant's ability to operate a commercial motor vehicle. In one embodiment, the weight values and determined scores may be stored in fields of the table 134.

In some embodiments, the system 100 may automatically select an algorithm corresponding to the full set of medical questions being administered to the applicant.

The system 100 may automatically flag responses in the full set of medical screening questions that have been programmed as being relevant to certification recommendations. The system 100 provides these flags to the medical examiner (e.g., via an output device 118 of the user device 110). In some embodiments, the system 100 may provide flags to a user if selected responses by the applicant are identified as being inconsistent. For example, responses may be flagged by the system 100 that are inconsistent relative to information already present in the system 100 regarding the applicant (e.g., based on responses from previous questions, based on results from previous medical examinations, and/or based on demographic information regarding the applicant acquired at operation 202) or regarding known medical diagnostic information.

In some embodiments, the system 100 may also provide a recommendation on the period of time before another medical examination is or should be required for the applicant based on the applicant's responses to the full set of screening questions. Stated in another way, based on the applicant's responses to the full set of screening questions, the system 100 may provide a recommended period of time that the applicant will be certified to operate a commercial vehicle. Accordingly, the applicant would need to be recertified before that time period has lapsed if the applicant wants to continue operating a commercial vehicle. This and other recommendations may be stored in the database 134 as well as in another database that refers to the database 132.

After scoring the full set of medical questions at operation 218, the system 100 may take the data from the full set of medical screening questions and store (e.g., associate) that data with the applicant's profile or in a database with a reference to the applicant's profile (e.g., at operation 214). In some embodiments, at operation 214, computerized reminders may be created in the system 100 regarding the applicant's profile (e.g., reminders of when to continue the medical examination, reminders to check on updates in the applicant's medical history, etc.).

At operation 220, potential limited certification (e.g., limited by length of certification time period) and/or disqualifying conditions are identified by the system 100 by automatically comparing known conditions with the responses of the applicant and available certification guidance stored in the system 100. For example, the system 100 may provide the medical practitioner or the entity who is requesting the CDME a summary of the findings along with the potential limited certification and/or disqualifying conditions along with the automated guidance from the system 100 (e.g., the numerical score and flags) and the recommended period of time before another medical certification is to be required of the applicant. In some embodiments, the system 100 may generate recommendations for prevention and/or treatment of any potentially disqualifying conditions.

At operation 222, the medical examiner may review the information provided by the system 100 and perform a direct (e.g., physical) examination of the applicant (e.g., results of blood pressure readings, vision tests, urinalysis, hearing tests, etc.). In some embodiments, recommendations or cues from the system 100 may act to guide or tailor the medical examiner's examination. Throughout the examination (or after), data input from the examiner or from associated medical equipment may be input (e.g., automatically or manually) into the system 100 and certification recommendation may be continually updated throughout the examination process. For example, the table 135 may include available examinations and procedures. Based on the results of the full medical exam questions and one or more medical examination protocols, the application 130 may populate the table 136 with a subset of examination procedures from the table 136. The system 100 may provide the examination procedures in the table 136 to the medical examiner. During the examinations and procedures in the 136 may be updated based on the medical examiner's inputted findings and medical examination protocols. For example, irrelevant procedures and examinations may be removed and new ones inserted into the table 136. Findings may also be stored in the table 136. Similarly, the system 100 may automatically update the applicant's profile in the system in real-time with the table 136 and the exam findings as they are input by the medical practitioners performing the exam. As discussed above, the system 100 may automatically populate a form with the entered information (e.g., in a comments section of the form) as new exam findings are entered into the system 100. These exam findings may be automatically compared with current known medical standards and guidance stored in the system 100. The recommendations from the system 100 (e.g., the numerical score and flags) and the recommended period of time before another medical certification is to be required of the applicant may be continuously generated and updated in real-time using the system 100.

In some embodiments, the user device 110 provided to the medical practitioner may include access to relevant guidance relating to the medical examination (e.g., medical sources, such as, FMCSA exam documentation, FMCSA Medical Review Board recommendations, FMCSA Medical Expert Panel recommendations, the Commercial Driver Medical Exam Handbook, and other peer reviewed research regarding any specific medical condition).

In some embodiments, the system 100 (e.g., via the user device 110) may update the tables 134 and 136 with additional probing questions regarding specific conditions, timing, and subsequent diagnostic testing and display the questions, based on previous information input into the system 100 directly by the medical examiner or from the questionnaires.

At operation 224, the system 100 may continually update all of the information stored on the applicant, including the table 134, table 136 and the applicant's profile, and continually provide new guidance, recommendations, and scoring as each new piece of data (and/or if previous data is amended by the examiner based on new findings) is input into the system (e.g., at operation 222) in an iterative process. As the data are inputted or amended at operation 222, the system 100 may also continue to automatically populate and update one or more related forms with the entered information as new exam findings or amended data are entered into the system 100.

At operation 226, the system 100 may generate additional questions (e.g., additional standardized questions) for the applicant, if necessary, based on the previous data into the system 100. For example, additional probing questions may be automatically selected by the system 100 and displayed on the user device 110 based on the health history responses and exam findings by the medical examiner. In some embodiments, such additional questions may be selected by the system 100 to differentiate between medical conditions that may be triggering two sets of guidance (e.g., conflicting sets of guidance). For example, conflicting guidance may be generated from the system 100 based on data from two or more of the initial questions, the full set of questions, and the physical exam and the additional questions may be selected to resolve that discrepancy.

At operation 228, the system 100 may automatically generate a final certification recommendation and provide that recommendation to the examiner (e.g., via the user device) once all data have been entered into the system 100. The final recommendation from the system 100 may include the maximum recommended period of time that the applicant may be certified based on the medical findings and corresponding guidance regarding the health conditions of the applicant uncovered in the above process. The final recommendation and associated data may be stored, along with the final certification time period from the examiner, which may differ from the time period previously recommended based on only the questionnaires, in the system at operation 214. In some embodiments, at operation 214, automatic reminders for reexamination may be created by the system 100.

While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of embodiments encompassed by the disclosure as contemplated by the inventors. While certain illustrative embodiments are described as a series of operations, no recitation of steps is meant to connote a requirement that the steps be performed in the order recited unless explicitly stated in this disclosure.

What is claimed is:

1. A system for managing a database for a medical examination, the system comprising:
    a non-transitory computer-readable storage medium storing at least one database and at least one software application;
    an electronic display; and
    a processor operably coupled with the electronic display and the non-transitory computer-readable storage medium, wherein the processor is configured, upon execution of the software application, to:
    display a user interface on the electronic display;
    receive, via one or more forms displayed via the user interface, input from an applicant for a license;
    create a user profile for the applicant based on the input;
    select, based on the user profile for the applicant and a type of the license, an initial set of medical questions for a medical certification for the license from a first table of the at least one database;
    insert the initial set of medical questions into a second table of the at least one database;
    present at the displayed user interface one or more of the initial set of medical questions stored in the second table;
    receive one or more answers from the applicant responsive to the initial set of medical questions;
    determine a first score for the applicant based on the one or more answers from the applicant;
    continually update the initial set of medical questions stored in the second table based on the one or more answers from the applicant responsive to the initial set of medical questions and the first score;
    present at the displayed user interface one or more of the continually updated initial set of medical questions stored in the second table;
    receive one or more additional answers from the applicant responsive to the updated initial set of medical questions;
    store the one or more answers from the applicant responsive to the displayed initial set of medical questions and the one or more additional answers from the applicant responsive to the displayed updated initial set of medical questions in the at least one database;
    responsive to storing the answers in the at least one database, select a second set of medical questions from the first table and insert the second set of medical questions into the second table;
    present at the displayed user interface one or more of the second set of medical questions stored in the second table;
    receive one or more answers from the applicant responsive to the second set of medical questions;
    continually update the second set of medical questions stored in the second table based on the one or more answers from the applicant responsive to the second set of medical questions;
    present at the displayed user interface one or more of the continually updated second set of medical questions stored in the second table;
    receive one or more additional answers from the applicant responsive to the updated second set of medical questions;
    determine a second score for the applicant based on the one or more additional answers from the applicant;
    store in the at least one database the one or more answers from the applicant responsive to one or more of the second set of medical questions and the one or more additional answers from the applicant responsive to the continually updated second set of medical questions;
    evaluate the stored one or more answers based on stored medical data;
    present at the displayed user interface one or more suggestions for examination for the medical certification to be performed by a medical examiner based on the stored one or more answers;
    generate a recommendation regarding whether the applicant should or should not receive the medical certification for the license based on the stored one or more answers, at least one of the first score and the second score, and input related to one or more medical examinations performed on the applicant by the medical examiner, the recommendation including a recommended period of time until a subsequent medical examination; and
    display the recommendation via the user interface.

2. The system of claim 1, wherein continually updating the second set of medical questions stored in the second table comprises:
    determining, based on at least one answer from the applicant and a questionnaire protocol for selecting from a plurality of medical examination questions, at least one question of the second set of medical questions stored in the second table to be deleted; and
    deleting the at least one question from the second table.

3. The system of claim 1, wherein continually updating the second set of medical questions stored in the second table comprises:
    determining, based on at least one answer from the applicant and a questionnaire protocol for selecting from a plurality of medical examination questions, at least one question stored in the first table to be inserted into the second table; and
    inserting the at least one question into the second table.

4. The system of claim 1, wherein the processor is further configured, upon execution of the software application, to store the answers in one or more answer fields of the second table, each answer field of the one or more answer fields associated with a question stored in the second table.

5. The system of claim 4, wherein the processor is further configured, upon execution of the software application, to store the second table in at least one database with the user profile.

6. The system of claim 1, wherein the processor is further configured, upon execution of the software application, to:
    tabulate at least one of the first score and the second score from one or more numerical values associated with one or more questions and answers stored in the second table; and
    store the at least one of the tabulated first score and the tabulated second score in at least one database with the user profile for the applicant.

7. The system of claim 6, wherein tabulating the at least one of the first score and the second score further comprises tabulating the at least one of the first score and the second score based on one or more numerical values associated with one or more medical conditions associated with the one or more questions and answers stored in the second table.

8. The system of claim 6, wherein the processor is further configured, upon execution of the software application, to:
select a subset of medical examinations from a third table, wherein the subset of medical examinations is selected responsive to one or more answers from the applicant stored in the second table and a medical examination protocol for selecting from a plurality of medical examinations associated with a plurality of medical conditions;
insert the subset of medical examinations into a fourth table;
present at the displayed user interface one or more of the subset of medical examinations stored in the fourth table; and
store in at least one database medical findings responsive to the presented one or more of the subset of medical examinations.

9. The system of claim 8, wherein the processor is further configured, upon execution of the software application, to store the medical findings in medical finding fields of the fourth table.

10. The system of claim 8, wherein the processor is further configured, upon execution of the software application, to continually update the medical examinations stored in the fourth table responsive to the medical findings stored in at least one database.

11. The system of claim 10, wherein continually updating the medical examinations stored in the fourth table comprises:
determining, based on at least one medical finding and the medical examination protocol, at least one medical examination stored in the third table to be inserted into the fourth table; and
inserting the at least one medical examination into the fourth table.

12. The system of claim 10, wherein continually updating the medical examinations stored in the fourth table comprises:
determining, based on at least one medical finding and the medical examination protocol, at least one medical examination to be deleted from the fourth table; and
deleting the at least one medical examination from the fourth table.

13. A system for managing a database for a medical examination, the system comprising:
a non-transitory computer-readable storage medium storing at least one database and at least one software application;
an electronic display; and
a processor operably coupled with the electronic display and the non-transitory computer-readable storage medium, wherein the processor is configured, upon execution of the software application, to:
display a user interface on the electronic display;
receive, via one or more forms displayed via the user interface, input from an applicant for a license;
select, based on the input and a type of the license, an initial set of medical questions from the at least one database;
insert the initial set of medical questions into a table of the at least one database;
present at the displayed user interface one or more of the initial set of medical questions stored in the table;
receive one or more answers from the applicant responsive to the initial set of medical questions;
determine a first score for the applicant based on the one or more answers from the applicant responsive to the initial set of medical questions;
present at the displayed user interface a suggestion to terminate the medical examination responsive to the first score indicating that the applicant is unlikely to pass the medical examination;
continually update the initial set of medical questions stored in the table based on one or more answers responsive to the initial set of medical questions;
present at the displayed user interface one or more of the continually updated initial set of medical questions stored in the table;
receive one or more answers from the applicant responsive to the updated initial set of medical questions;
determine a second score for the applicant based on the one or more answers from the applicant responsive to the updated initial set of medical questions;
store answers responsive to the displayed initial set of medical questions and the updated initial set of medical questions in at least one database; and
present at the displayed user interface a recommendation regarding whether the applicant should receive a certification for the license based on the stored answers, the first score, and the second score.

14. A method of managing at least one database for a medical examination, the method comprising:
selecting an initial set of medical questions from medical questions stored at a first table of the at least one database based on an applicant and a type of a license desired by the applicant;
inserting the initial set of medical questions into a second table of the at least one database;
continually updating the initial set of medical questions stored in the second table based on one or more answers from the applicant responsive to the initial set of medical questions;
determine one or more scores for the applicant based on the one or more answers;
storing the one or more answers in the at least one database;
generate a medical certification recommendation whether or not the applicant should pass the medical examination based on the one or more answers and the one or more scores; and
storing the medical certification recommendation for the license in the at least one database.

15. The method of claim 14, wherein continually updating the initial set of medical questions stored in the second table comprises:
determining, based on at least one answer and a questionnaire protocol for selecting from a plurality of medical examination questions, at least one question stored in the first table to be inserted into the second table; and
inserting the at least one question into the second table.

16. The method of claim 14, wherein continually updating the initial set of medical questions stored in the second table comprises:
determining, based on at least one answer and a questionnaire protocol for selecting from a plurality of medical examination questions, at least one question stored in the second table to be deleted; and
deleting the at least one question from the second table.

17. The method of claim 14, further comprising:
selecting a subset of medical examinations from a third table, wherein the subset of medical examinations is selected responsive to one or more answers stored in the second table and a medical examination protocol for selecting from a plurality of medical examinations associated with a plurality of medical conditions;
inserting the subset of medical examinations into a fourth table;
continually updating the medical examinations stored in the fourth table based on findings received responsive to at least one of the medical examinations; and
storing in at least one database the received responsive findings.

18. The method of claim 14, further comprising:
tabulating the one or more scores from one or more numerical values associated with the initial set of medical questions and the one or more answers stored in the second table; and
storing the tabulated one or more scores in at least one database with a user profile.

19. The method claim 18, wherein tabulating the one or more scores further comprises tabulating the one or more scores based on one or more numerical values associated with one or more medical conditions associated with the initial set of medical questions and the one or more answers stored in the second table.

20. The method of claim 14, further comprising storing the one or more answers in the second table.

* * * * *

UNITED STATES PATENT AND TRADEMARK OFFICE
CERTIFICATE OF CORRECTION

PATENT NO. : 10,825,555 B2
APPLICATION NO. : 15/451018
DATED : November 3, 2020
INVENTOR(S) : Matthew S. Thiese et al.

Page 1 of 1

It is certified that error appears in the above-identified patent and that said Letters Patent is hereby corrected as shown below:

On the Title Page

In ITEM (73), Line 1, change "Safe Lane Health, Inc.," to --SafeLane Health, Inc.,--

Signed and Sealed this
Twenty-ninth Day of December, 2020

Andrei Iancu
*Director of the United States Patent and Trademark Office*